(12) United States Patent
Bulsink et al.

(10) Patent No.: US 6,514,467 B1
(45) Date of Patent: Feb. 4, 2003

(54) AIR-FRESHENER

(75) Inventors: Dirk Jan Bulsink, Leiden (NL); Johannes Arnoldus van Voorden, Zoetermeer (NL); Johannes Antonius Gerardus Wilhelmus Zigmans, Rotterdam (NL)

(73) Assignee: Sara Lee/DE N.V., Utrecht (NL)

( * ) Notice: Subject to any disclaimer, the term of this patent is extended or adjusted under 35 U.S.C. 154(b) by 0 days.

(21) Appl. No.: 09/511,054

(22) Filed: Feb. 23, 2000

(30) Foreign Application Priority Data

Feb. 25, 1999 (NL) .......................................... 99200559

(51) Int. Cl.[7] ................................................. A62B 7/08
(52) U.S. Cl. ......................... 422/122; 239/54; 239/59; 422/123
(58) Field of Search ............................... 422/122, 123; 239/59, 54

(56) References Cited

U.S. PATENT DOCUMENTS

| | | | |
|---|---|---|---|
| 4,621,768 A | | 11/1986 | Lhoste et al. |
| 4,840,773 A | | 6/1989 | Wade |
| 4,950,457 A | * | 8/1990 | Weick .......................... 422/123 |
| 5,368,822 A | * | 11/1994 | McNeil ....................... 422/124 |
| 5,373,581 A | * | 12/1994 | Smith .......................... 392/390 |
| 5,422,078 A | * | 6/1995 | Colon ......................... 422/123 |

FOREIGN PATENT DOCUMENTS

FR    2 695 305    3/1994

* cited by examiner

Primary Examiner—Krisanne Thornton
(74) Attorney, Agent, or Firm—Merchant & Gould, P.C.

(57) ABSTRACT

An air-freshener for a vehicle, in particular a motorcar, provided with a housing into which a container for a volatile liquid or a liquid containing one or more volatile components can be inserted, in the opening of which container a wick extending into the housing is fitted. There are further present a covering cap which, when the container with wick has been inserted into the housing, is movable up and down over the wick, and control means for setting the position of the covering cap.

12 Claims, 4 Drawing Sheets

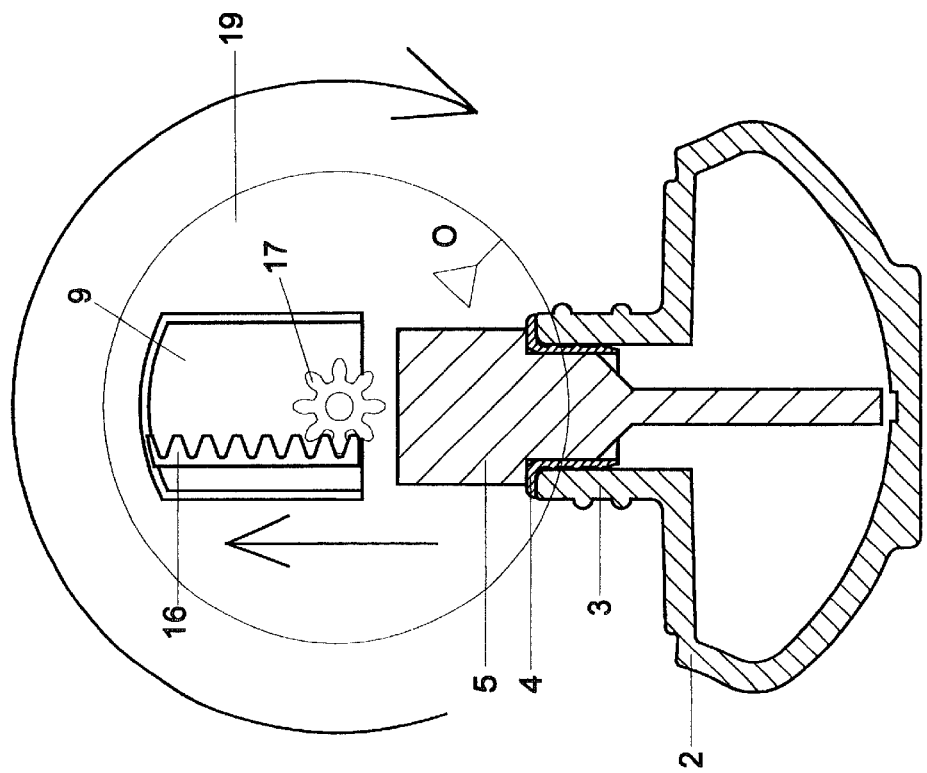
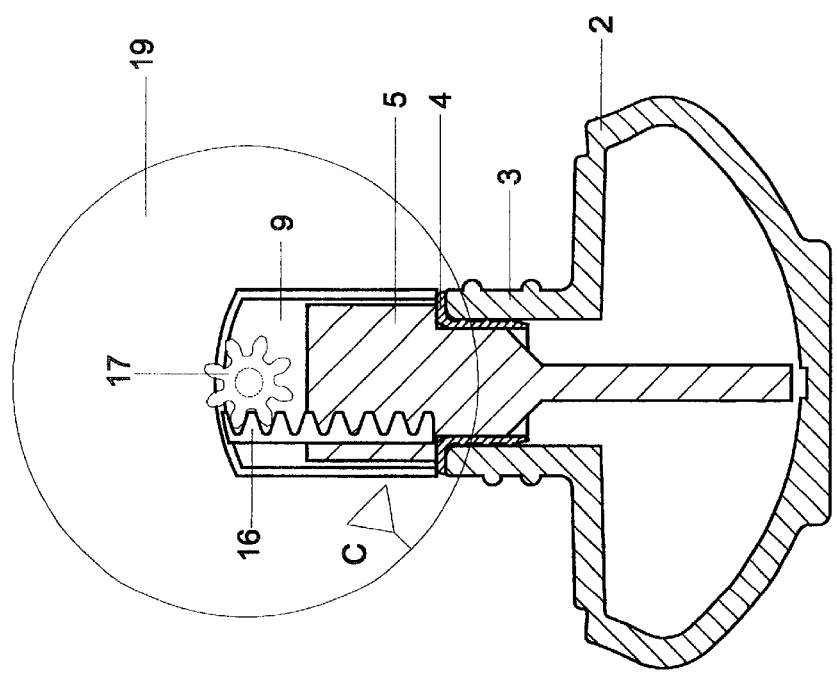

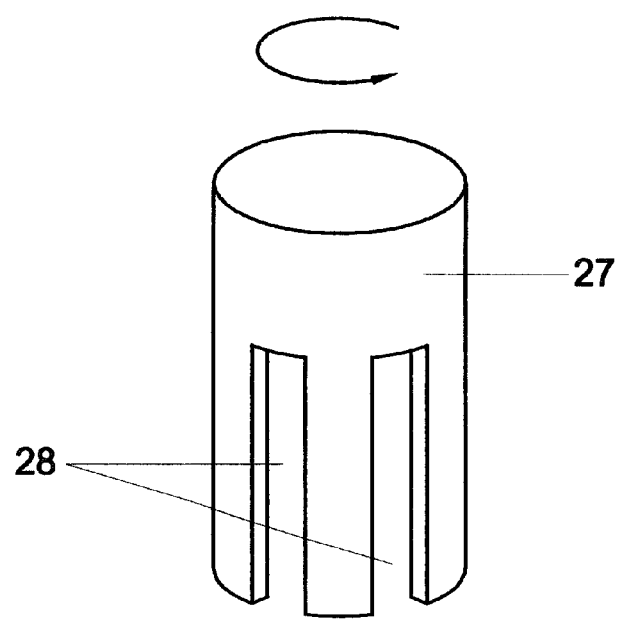
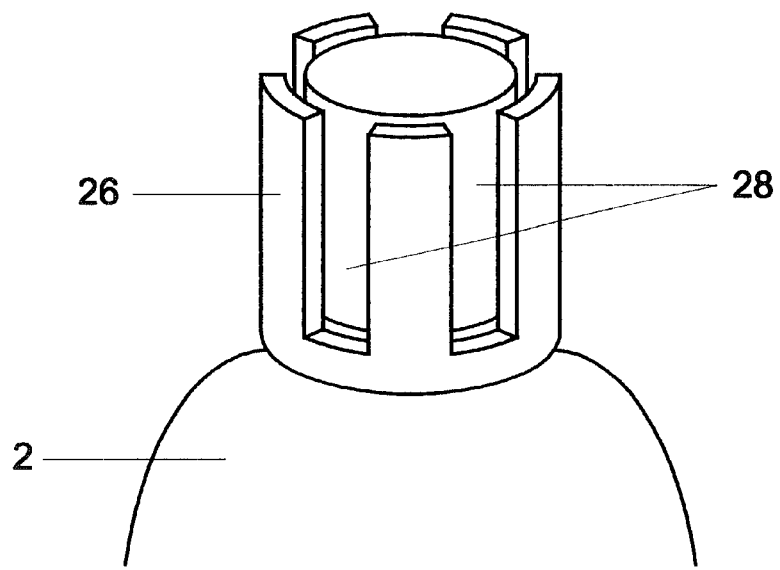
Fig. 6

AIR-FRESHENER

The present invention relates to an air-freshener for a vehicle, in particular a motorcar.

There is a need for providing a pleasant air also in vehicles. For that reason, air-fresheners are on the market which can be disposed in a motorcar, for instance on a guard of the fan in the dashboard thereof.

The object of the invention is to provide an air-freshener that operates efficiently and reliably and lasts for a long time.

To that end, in accordance with the invention, there is provided an air-freshener for a vehicle, in particular a motorcar, provided with a housing into which a container for a volatile liquid or a liquid containing one or more volatile components can be inserted, in the opening of which container a wick extending into the housing is fitted, and with a movable covering cap which, when the container with wick has been inserted into the housing, can cover the wick entirely or partially, and with control means for setting the position of the covering cap.

Hence, in the air-freshener, each time when a container, in particular a flask, containing a volatile liquid or a liquid having one or more volatile components, is empty, another, filled, container can be inserted into the air-freshener, as a result of which the air-freshener itself can last for a particularly long time. The air-freshener is out of action when the covering cap has covered the wick entirely. When the covering cap has been removed from the wick entirely or partially, the liquid absorbed from the container by the wick can readily evaporate. Thus, an efficient and reliable operation of the air-freshener is obtained.

In a favorable embodiment, the covering cap, when the container with wick has been inserted into the housing, can be moved up and down over the wick.

To enable an air flow that facilitates the evaporation of the liquid absorbed into the wick, the housing is provided with ventilating openings via which, when a container with a wick extending in the housing has been fitted, air can flow along the entirely or partially released wick.

In a favorable embodiment, the control means for positioning the covering cap are formed by a gear rack fitted on the covering cap and a gear engaging therewith, which gear is connected to a control member. In particular, this control member is formed by a turning knob which closes the housing and which is provided with ventilating openings. In particular the turning knob provides that virtually no pulling forces are exerted on the air-freshener, whereby the air-freshener could possibly be pulled from its place of attachment, which, when placed in a motorcar, might create dangerous situations in that the driver of the car may wish to fix the air-freshener again during driving.

To enable an optimal air flow through the air-freshener, further ventilating openings have been provided in the wall of the housing located opposite the turning knob. In particular, the covering cap is movable up and down between the turning knob and the opposite wall of the housing. As a result, when the container with the wick extending in the housing has been inserted and the covering around the wick has been removed entirely or partially, an optimal air flow along the wick is possible.

The air-freshener comprises a clip element to enable securing the air-freshener on a strip-shaped element, in particular that of a guard of the fan in the dashboard of a motorcar. This makes it possible to utilize the air flow from the fan for the air-freshener. This means that the air-freshener is not only controllable by positioning the covering cap by means of the turning knob, but also by controlling the air flow through the guard of the fan, i.e. by switching the fan of the vehicle to which the air-freshener is connected faster or slower and/or by switching the temperature of the air flow in the vehicle higher or lower. In particular, it is pointed out that the air-freshener operates properly only after the fan has been switched on.

The clip element for fixing the air-freshener in the vehicle preferably comprises four resilient clamping elements projecting outwards from the housing, which clamping elements are separated from each other according to two planes which are at least substantially perpendicular to each other, to enable securing the air-freshener either on a vertical, or on a horizontal strip-shaped element. Due to the resilient action of the clamping elements, the air-freshener can readily, yet sufficiently firmly be secured on, for instance, the guard of a car fan. A good clamping action is obtained particularly when the resilient elements are formed by metal strips; in that case, to prevent damage, these strips have at least their ends provided with a plastic covering layer.

Because the air-freshener can each time be supplied with a new container, it is favorable when the housing comprises a holding element for fixedly holding or clamping an insertable and removable container for a volatile liquid or a liquid having one or more volatile components.

The invention does not only relate to an air-freshener, but also to a container for a volatile liquid or a liquid having one or more volatile components, in the opening of which a wick can be placed, which container has a shape fitting in the air-freshener, as described hereinabove. After all, as far as design and dimensions are concerned, the container and the wick should be adjusted to the concrete construction of the air-freshener. The invention further relates to an air-freshener as described hereinabove, comprising a container adjusted thereto.

The invention will now be specified with reference to the accompanying drawings. In these drawings:

FIG. 4 shows the control means for setting the covering cap in the air-freshener, with the wick being completely covered;

FIG. 5 shows the same control means as in FIG. 4, with the covering cap being raised completely and the wick thus being entirely free; and FIG. 6 shows an alternative embodiment for setting the position of the covering cap.

Figure 1:
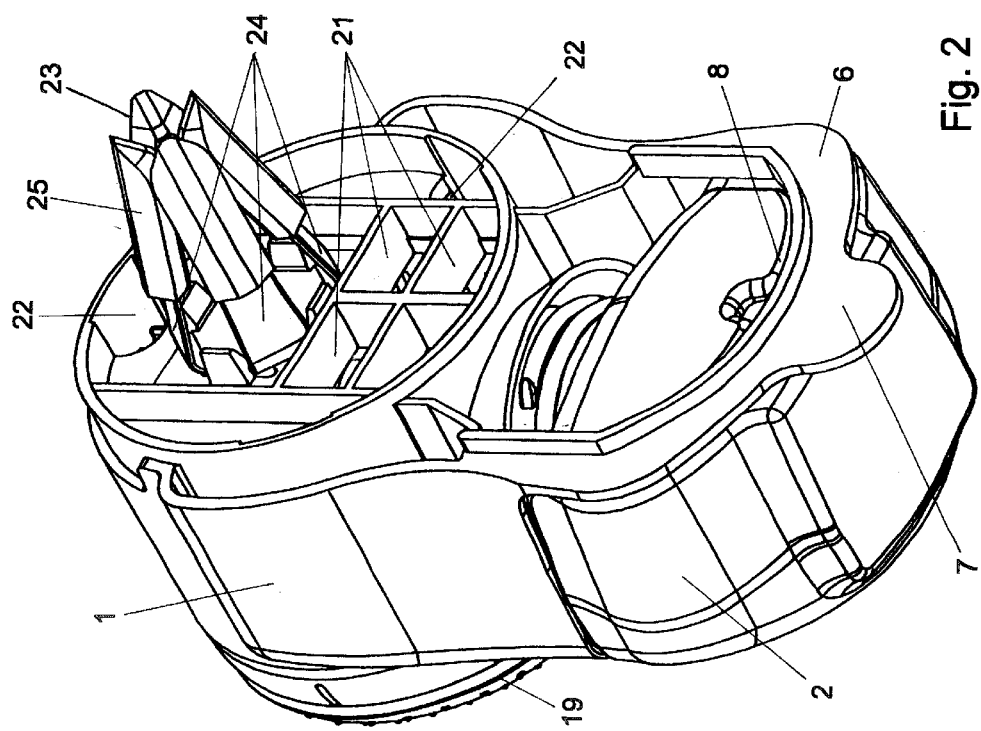
FIG. 1 is a perspective front view of the air-freshener with a container inserted therein.
Figure 2:
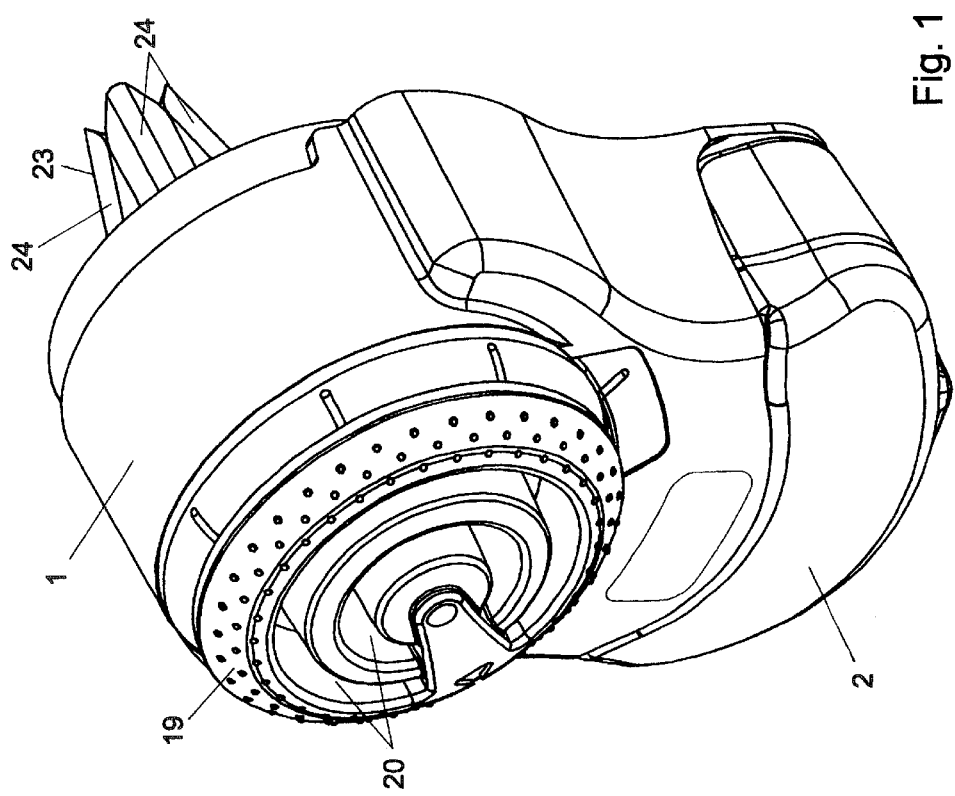
FIG. 2 is a perspective rear view of this air-freshener with container.
Figure 3:
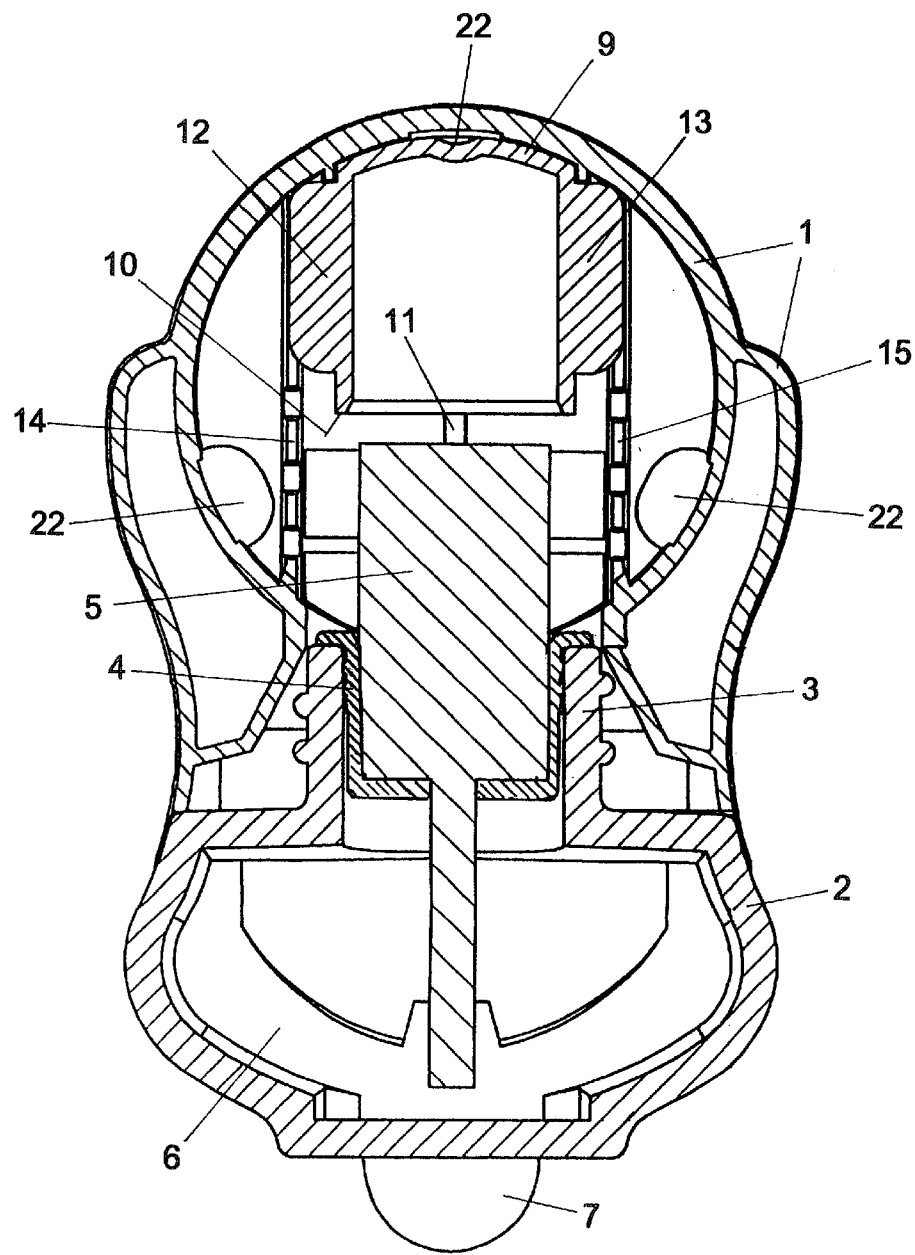
FIG. 3 shows a longitudinal section of the air-freshener in FIGS. 1 and 2.

The air-freshener shown in FIGS. 1–3 comprises a housing 1, having placed therein a container 2 for a volatile liquid or a liquid having one or more volatile components. Here, the container 2 has the shape of a glass flask having a neck 3 in which a sealing sleeve 4 for a wick 5 is provided. By this wick, a liquid in the flask is soaked up, while from the upper portion of the wick 5, i.e. the portion thereof projecting from the neck 3 of the flask 2, the soaked-up liquid or the volatile components present therein, can evaporate. On the rear side, the housing 1 has an annular portion 6 with, on the lower side thereof, a holding element 7 in the form of a lip. On the rear side, the flask 2 has, adjacent the lower end thereof, a projecting edge 8 which, when the flask 2 has been placed in the housing 1, projects rearwards above the lip, so that the flask 2 remains in the position in which it has been inserted into the housing 1. By bending the annular portion 6 rearwards, the flask 2 can be pulled from the housing 1. Located in the housing 1 is a covering cap 9 in the form of a sleeve-shaped body. This sleeve-shaped body 9 is closed off at its top side, but open at the bottom side, and has a diameter such that it fits easily over the wick part projecting into the housing 1. In the upper position, shown in FIG. 3, of the sleeve-shaped body 9, the upper portion of the wick is completely uncovered, while when the sleeve-shaped body 9 is moved into the lowermost position, the wick 5 is completely covered; in this position, the lower edge 10 of the sleeve-shaped body 9 connects to the top side of the sealing sleeve 4. To prevent the sleeve-shaped body 9 from possibly turning around its longitudinal axis within the housing, a projecting ridge has been provided over the entire length of the sleeve-shaped body, which ridge fits in a corresponding groove 11 in the rear wall of the housing. Further, the sleeve-shaped body 9 is to that end provided with two projecting strips 12 and 13 resting against forwardly projecting strips 14 and 15 respectively, provided on the rear wall of the housing. On the front side, a gear rack 16 is provided on the sleeve-shaped body 9, in the longitudinal direction thereof, and provided parallel thereto is a support edge. This gear rack cooperates with a gear 17 fixedly provided on the inside of a turning knob 19 that forms a part of the front side of the housing 1. By turning the turning knob 19, the sleeve-shaped body 9 is moved up and down in the housing 1 and the wick 5 is fully covered or fully or partially released. The turning knob 19 is marked "C" (closed) and "O" (open), to indicate that the sleeve-shaped body 9 has been slid down over the wick 5 completely, or, respectively, has been moved up completely.

In the housing 1, ventilating openings are provided on the front and rear sides thereof. Located in the turning knob 19 are ventilating openings 20 having the shape of segments of a circle, while in the rear wall of the housing, rectangular ventilating openings 21 are provided, as well as some further openings 22. The rectangular ventilating openings 21 in the rear wall of the housing are provided directly behind the wick part that extends into the housing, enabling an air flow through these rectangular openings 21 along the wick 5 or the sleeve-shaped body 9 and through the openings 20 in the turning knob. Of course, this will only involve an evaporation of liquid or a liquid component from the wick 5 if this wick has been entirely or partially released by the sleeve-shaped body 9, i.e. if the sleeve-shaped body 9 has been entirely or partially displaced upwards by means of the turning knob 19. Such air flow is obtained in particular when the air-freshener is arranged on a fan, for instance on the guard strips or strip-shaped elements of a car fan that are usually located on the dashboard of the car. The invention provides a clip element 23 for securing the air-freshener on such strip-shaped element. The clip element 23 comprises four clamping elements 24 projecting outwards from the housing 1, which clamping elements are separated from each other according to two planes which are at least substantially perpendicular to each other, to enable the air-freshener to be secured either on a horizontal, or on a vertical strip-shaped element. The clamping elements 24 are formed by metal strips provided, at the ends thereof, with a plastic covering layer 25.

The invention is not limited to the exemplary embodiment here described with reference to the drawings, but comprises all kinds of modifications thereto, of course in so far as they fall within the protective scope of the following claims. In particular, it is pointed out that all kinds of alternative control means and operating knobs can be used. For instance, it is possible to provide, in the front wall of the housing 1, a knob that can be slid up and down, by means of which knob the sleeve-shaped body 9 can then be moved along. It is also possible to provide the outer side of the sleeve-shaped body 9 with a screw thread fitting in a sleeve having mating screw thread, which sleeve projects from the housing and can be rotated manually. Also, the covering cap, as shown in FIG. 6, can be formed by two sleeve-shaped bodies 26 and 27 which are rotatable independently of each other and which are provided with ventilating grids 28. In FIG. 6, the sleeve-shaped body 26 is fixed in the housing and connected to the container 2, while the sleeve-shaped body 27 is rotatable to open or close the ventilating grids completely or partially, depending on the angular position of this body. Further, the sleeve-shaped body 27 projects from the housing at the top side and can thus readily be operated by hand. Depending on the type of control means and the design of the housing 1, the turning knob can further be provided in the front wall, the sidewall or at the top side of the housing. Also, the openings in the front and rear walls of the housing 1 may have any desired shape. The flask may likewise be given any suitable shape, as long as it can be placed and fixed in the housing 1.

What is claimed is:

1. An air-freshener for a vehicle provided with a reusable housing into which a container containing a volatile liquid or a liquid containing one or more volatile components is insertable, the container being provided with a wick which extends with an evaporating part into the housing when the container is inserted in the housing, the housing being provided with a movable covering cap and with control means for setting a position of the covering cap relative to the evaporating part of the wick, wherein the covering cap snugly fits around the evaporating part of the wick and wherein the covering cap can cover the wick entirely or partially depending on the position of the covering cap relative to the wick.

2. An air-freshener according to claim 1, wherein, when the container with the wick has been inserted into the housing, the covering cap is movable up and down over the wick.

3. An air-freshener according to claim 1, wherein the housing defines ventilating openings via which, if the wick is arranged to extend in the housing, air can flow along the wick.

4. An air-freshener according to claim 1, wherein the control means are formed by a gear rack provided on the covering cap and a gear engaging with said gear rack and connected to a control member.

5. An air-freshener according to claim 4, wherein the control member is formed by a turning knob closing the housing, in which turning knob ventilating openings are defined.

6. An air-freshener according to claim 5, wherein ether ventilating openings are defined in a wall of the housing located opposite the turning knob.

7. An air-freshener according to claim 6, wherein the covering cap is movable up and down between the turning knob and the wall of the housing opposite thereto.

8. An air-freshener according to claim 1, further comprising a clip element for securing the air-freshener on a strip-shaped element.

9. An air-freshener according to claim 8, wherein the air-freshener is configured so that, when the air-freshener is connected to a fan of the vehicle, the air flow through the air-freshener is controllable by setting the position of the covering cap, by switching the fan of the vehicle faster or slower, and by switching the temperature of the air flow in the vehicle higher or lower.

10. An air-freshener according to claim 8, wherein the clip element comprises four clamping elements projecting outwards from the housing, the clamping elements being separated from each other according to two planes which are at least substantially perpendicular to each other, to enable securing the air-freshener either on a vertical, or on a horizontal strip-shaped element.

11. An air-freshener according to claim 10, wherein the clamping elements are formed by metal strips provided, at least at the ends thereof, with a plastic covering layer.

12. An air-freshener according to claim 1, wherein the housing comprises a holding element for retaining the container.

* * * * *